United States Patent [19]

Haynes

[11] Patent Number: 4,503,385
[45] Date of Patent: Mar. 5, 1985

[54] APPARATUS AND METHOD FOR REGULATING SHEATH FLUID FLOW IN A HYDRODYNAMICALLY FOCUSED FLUID FLOW SYSTEM

[75] Inventor: John L. Haynes, Chapel Hill, N.C.

[73] Assignee: Becton, Dickinson and Company, Paramus, N.J.

[21] Appl. No.: 512,267

[22] Filed: Jul. 11, 1983

[51] Int. Cl.³ .......................................... G01N 27/00
[52] U.S. Cl. .................................................. 324/71.4
[58] Field of Search .................... 324/71.4; 73/432 PS, 73/61 R

[56] References Cited

U.S. PATENT DOCUMENTS

| Re. 28,558 | 9/1975 | Hogg | 324/71.4 |
| 3,746,976 | 7/1973 | Hogg | 324/71.4 |
| 4,070,617 | 1/1978 | Kachel et al. | 324/71.4 |
| 4,110,604 | 8/1978 | Haynes et al. | 324/71.4 X |
| 4,165,484 | 8/1979 | Haynes | 324/71.4 |
| 4,240,029 | 12/1980 | Haynes | 324/71.4 |
| 4,434,398 | 2/1984 | Berg et al. | 324/71.4 |

OTHER PUBLICATIONS

*Introducing the Ultra-Flo 100 Whole Blood Platelet Counter* Clay Adams Lab Instr. Brochure Feb. 1979.

Primary Examiner—Gerald Goldberg
Assistant Examiner—Joseph W. Roskos
Attorney, Agent, or Firm—Richard J. Rodrick

[57] ABSTRACT

An apparatus for analyzing particles, adapted to operate continuously even in the absence of particles contained in a sample medium, includes a sensing region and a particle analyzer associated therewith. A fluid flow path, preferably air flow, causes a sample medium with particles therein to flow through the sensing region. Another fluid flow path ensheathes the sample medium with a flowing sheath fluid for hydrodynamically focusing the particles as they pass through the sensing region. The sheath fluid is adapted to flow at a first flow rate compatible with the flow rate of flowing particles. When the apparatus is operating in the absence of a sample medium, the sheath fluid is controlled to flow at a second flow rate, slower than the first flow rate, for collection thereof.

16 Claims, 6 Drawing Figures

APPARATUS AND METHOD FOR REGULATING SHEATH FLUID FLOW IN A HYDRODYNAMICALLY FOCUSED FLUID FLOW SYSTEM

BACKGROUND OF THE INVENTION

1. Field of the Invention

The present invention relates to an apparatus and method for analyzing particles in a continuous operation even when particles are not present, and more particularly, concerns an apparatus and method for regulating sheath fluid flow in a hydrodynamically focused fluid flow system.

2. Description of the Prior Art

There are a number of cell or particle analyzing devices employing flow cytometry techniques which rely on hydrodynamically focused fluid flow through an aperture for determining specific characteristics of the flowing cells or particles. Flow analysis of particles has been employed in the determination of a variety of characteristics of individual particles. This analysis is most useful in analyzing or determining characteristics of cells for the collection of information which would be useful in areas of research, hematology, immunology and the like. The researcher, for example, may be interested in determining specific characteristics of individual cells so that such cells may be classified, identified, quantified, and perhaps sorted for further investigations or analysis.

Three devices which rely on hydrodynamically focused fluid flow systems are sold by Becton, Dickinson and Company. One device, known as the ULTRA-FLO 100 TM Whole Blood Platelet Counter, rapidly and reliably counts whole blood platelets in the hematology laboratory. In the ULTRA-FLO 100 system, a trajectory of a diluted sample containing platelets passes straight through the center of the counting chamber orifice since the sample fluid is focused by a sheath of pressurized fluid. Another device sold by Becton, Dickinson and Company, relying on a hydrodynamically focused fluid flow system, is known as the FACS TM analyzer. The FACS analyzer rapidly analyzes cells on the basis of fluorescence and electronic volume properties. Analysis is accomplished by introducing cells in suspension to the center of a focused liquid stream and causing them to pass, one at a time, through the filtered and focused light from a high-power mercury-arc lamp. Each cell is individually characterized by its electronic impedance volume and by the intensity and color of fluorescence emitted while it is illuminated. Another device known as the FACS TM sorter operates on principles similar to the FACS TM analyzer, but further sorts the cells based on specifically detected characteristics. In all of the aforementioned systems, a sheath fluid is utilized to focus the particles or cells as they pass through the aperture associated with the analyzing or counting capabilities. U.S. Pat. Nos. 4,240,029, 4,165,484 and 4,110,604 describe particle analysis systems in which particles flowing in a stream are enveloped in a sheath fluid which focuses and confines the sample fluid (with particles) to the center of the flowing stream.

When a sheath fluid is used in a hydrodynamically focused fluid flow system, the sheath fluid is normally stored in a reservoir from which it is withdrawn during the operation of the device to ensheathe the sample fluid having the particles to be analyzed contained therein. Oftentimes in these types of analysis systems or equipment, the apparatus is turned on either just prior to or at the time the first sample of fluid is to be tested. When a sample has been tested in the analyzer, counter or the like, the sample is normally removed while the equipment remains operating. If the equipment is operating continuously, the sheath fluid normally flows at the same rate irrespective of whether a sample fluid is being tested or not. As a result, during changes between samples or during any delays, sheath fluid might normally drain from the equipment when the sample is not in position. This causes the supply of sheath fluid in the reservoir to become depleted more quickly and without benefit if it drains from the equipment when a sample is not being tested. Of course, the sheath fluid may be collected as it drains from the equipment for subsequent use. However, this could require the shut down of the equipment to restore the collected sheath fluid back to the reservoir for such subsequent use. Filtering the fluid can also be accomplished so that the fluid can be re-used in the equipment.

U.S. Pat. No. 4,070,617 discloses an apparatus for controlling the particle flow when measuring the properties of particles suspended in liquid. This patented invention includes a container for storing the particle-free electrolyte and a drip chamber into which fluid from the container drips. The drip chamber is adjustable thereby allowing an adjustment in the pressure difference between the particle suspension liquid and the particle-free electrolyte carrier. By adjusting this pressure differential, flowrate of the particle suspension into the electrolyte carrier can be controlled. However, the invention of U.S. Pat. No. 4,070,617 does not satisfy the needs of a system such as described above. U.S. Pat. No. Re. 28,558 discloses an apparatus for studying physical properties of particles passing through a screening aperture and carried in suspension, wherein a sheath fluid is employed and is re-used in the closed, recirculating system.

It is desirable to have a minimum change in the fluid level in the sheath reservoir of a hydrodynamically focused system particularly since the variations in the sheath fluid level affect the differential pressure between the sheath and sample fluid, which in turn affects the sample flow rate. Further, it would also be desirable to provide a system where the sheath flow rate is reduced or minimized during periods when no sample is present for analysis, but while the equipment is still operating. It is toward the satisfaction of the aforementioned desired achievements that the present invention is directed.

SUMMARY OF THE INVENTION

An apparatus of the present invention for analyzing particles, adapted to operate continuously even in the absence of particles in a sample medium, comprises a sensing region and particle analyzing means associated therewith. Means causes a sample medium with particles therein to flow through the sensing region. Means for ensheathing said sample medium with a flowing sheath fluid hydrodynamically focuses the particles as they pass through the sensing region. The sheath fluid is adapted to flow at a first flow rate compatible with the flow rate of flowing particles. Means are provided for flowing the sheath fluid at a second flow rate, slower than the first rate when the apparatus is operating in the absence of a sample medium.

In a preferred embodiment of this aspect of the present invention, a hydrodynamically focused fluid flow system is improved. Such system has an aperture through which particles to be analyzed flow. Air flow means are associated with a sample fluid containing the particles and for causing the particles to flow through the aperture. Sheath fluid flow means provide a flow of sheath fluid around the particles for focusing the particles which flow through the aperture. Means analyzes the particles which flow through the aperture. In this system, the improvement comprises an antechamber in fluid communication with the air flow means, sheath fluid flow means and a sheath fluid reservoir containing sheath fluid. This reservoir is also in fluid communication with the air flow means. Included in the antechamber is a first operable valve which allows sheath fluid to flow from the reservoir to the antechamber but restricts reverse flow if the pressure in the antechamber is higher than the pressure in the reservoir. Also included in the antechamber is a second operable valve which closes when the antechamber is full of sheath fluid and prevents sheath fluid from flowing into the air flow means. Thus, flow of sheath fluid toward the aperture and flow of air for forcing the particles from the sample fluid through the aperture in a hydrodynamically focused flow is established.

In another aspect of the present invention, a continuously operating method for intermittently analyzing particles comprises flowing a sample medium with particles therein through a sensing region. This method includes analyzing the particles for specific characteristics thereof. In accordance with this method, the sample medium is ensheathed with a flowing sheath fluid for hydrodynamically focusing the particles as they pass through the sensing region. The sheath fluid flows at a first flow rate compatible with the flow rate of flowing particles. This method includes flowing the sheath fluid through the sensing region at a second flow rate, slower than the first flow rate, when there is no sample medium being analyzed.

In accordance with the principles of the present invention, a number of significant features and advantages are achieved. For instance, the present invention will provide a more constant sheath fluid pressure. Accordingly, variations in the liquid level in the sheath fluid reservoir should not affect the sheath fluid pressure. Only variations in the fluid level in the antechamber, which can be made arbitrarily small, should affect the sheath fluid pressure associated with the aperture through which the sheath fluid flows. In addition, the air pressure on the fluid sample and the antechamber should be identical in the preferred embodiment of the present invention. If there is an air leak at the fluid sample seal, it would cause an equal pressure loss in the sheath fluid and tend to equalize fluid flow. Moreover, since the sheath fluid reservoir need only be pressurized to one psi or less, the mechanical requirements for strength and the time required to pressurize a nearly empty reservoir would be reduced. Since the pressure in the reservoir is not critical, the one psi pressure regulator need not be sophisticated. Along the same lines, the preferred valves used in the antechamber may be self-actuating with the seals on each being noncritical.

Of most significance in the present invention is the reduction in sheath fluid usage during operation of the particle analyzing apparatus. When a sample fluid is not in position on the apparatus, the flow of sheath fluid is reduced to a rate which can be made significantly low, thereby reducing the consumption of sheath fluid, allowing the use of a smaller reservoir or longer run time before reservoir changes. This advantage represents an improvement over the sheath fluid flow features of the apparatus described in U.S. Pat. No. 4,240,029. Of course, when a sample fluid is in position on the analyzing apparatus, sheath fluid flow occurs at a rate which is faster and is compatible with the rate of particle flow through the analyzing aperture in the apparatus.

DETAILED DESCRIPTION

Figure 1:
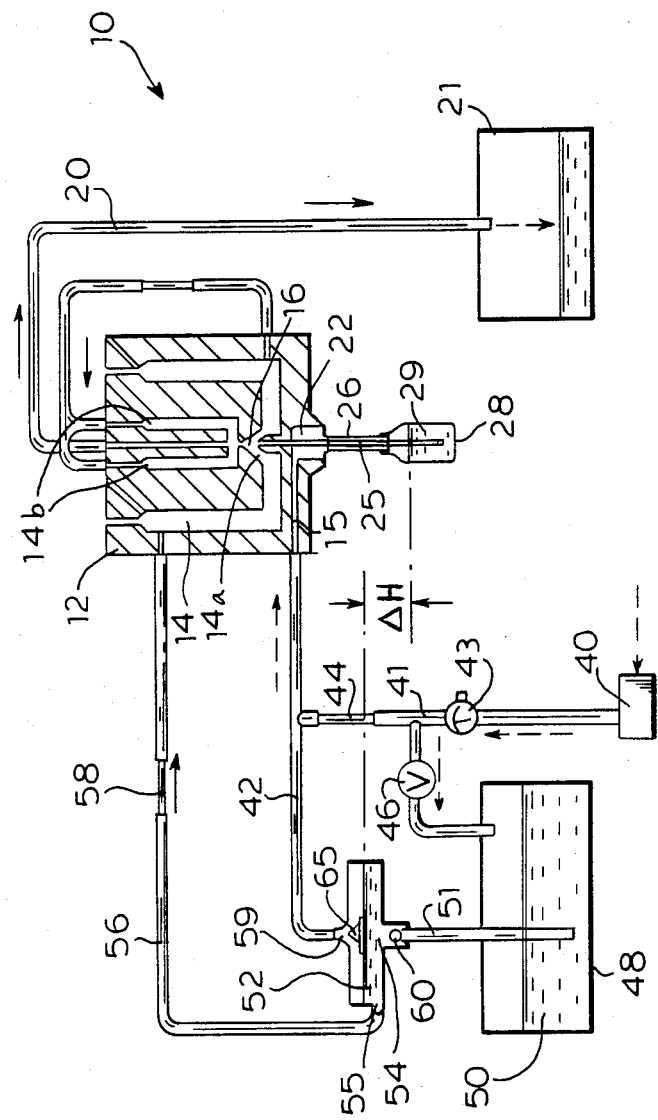
FIG. 1 is a schematic representation of the preferred fluid channels of the particle analyzing apparatus of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 2:
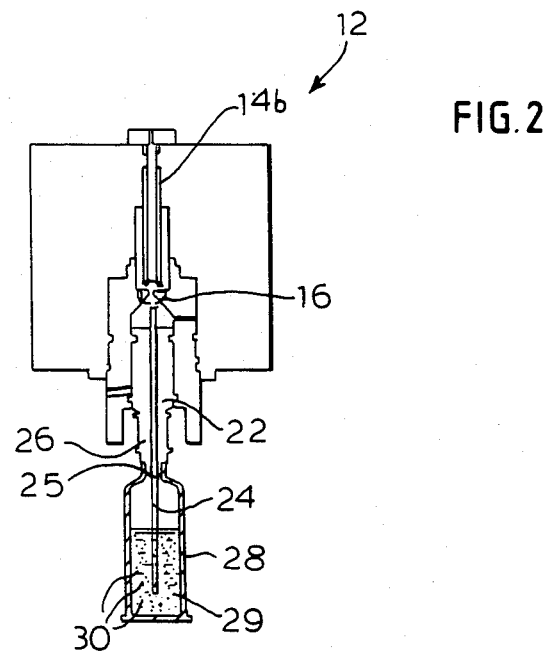
FIG. 2 is an enlarged side elevational view of the connection of a sample fluid to the fluid channels of the particle analyzing apparatus of FIG. 1.
Figure 3:
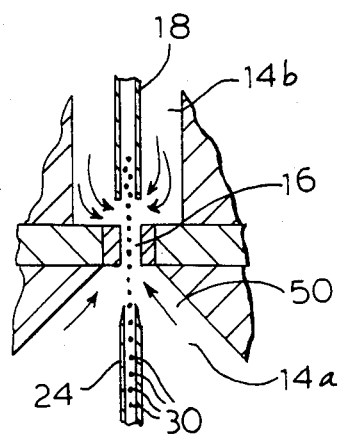
FIG. 3 is a further enlarged view of the aperture sensing region and the fluid channels of the preferred particle analyzing apparatus.

Adverting to the drawings, and FIG. 1 in particular, there is illustrated the preferred fluid channel paths of an apparatus 10 for regulating sheath fluid flow in a hydrodynamically focused fluid flow system. In the schematic representation of FIG. 1, the heart of apparatus 10, as regards the fluid flow channels therethrough, is a chamber 12 through which fluids flow for analyzing certain parameters of particles using flow cytometry techniques. There are two separate flow paths through chamber 12, a liquid flow channel 14 and an air flow channel 15. Liquid flow channel 14 is divided into two segments: a first segment 14a for delivering front sheath fluid through chamber 12 and segment 14b for providing a back sheath fluid through chamber 12. Separating the fluid channel segments is an aperture 16 as more clearly seen in FIGS. 2 and 3 taken in conjunction with FIG. 1. Aperture 16 may be a Coulter-orifice or other controlled opening through which particles contained in a liquid stream flow for analysis of certain characteristics of the particles. Various elements, preferably electrically operated, are associated with the aperture, and although not shown in the drawings, provide a mechanism for analyzing the particles which flow through the aperture. With regard to the aperture and chamber arrangement as illustrated in FIGS. 1 to 3, one particle analyzing feature is that of counting particles in a liquid suspension as more clearly described in U.S. Pat. No. 4,240,029.

As seen in FIG. 1, sheath fluid flows through channels 14a and b as depicted by the solid arrows. After sheath fluid flows through aperture 16, the fluid and particles passing through the aperture travel into a narrow tube 18. This narrow tube is connected to a somewhat larger flow line 20 which directs the used sheath fluid and particles into a collection container 21. It is appreciated that only sheath fluid will be collected into container 21 when the apparatus is operating without a particle sample in position.

Air channel 15 terminates in an air outlet port 22. Extending through port 22 and terminating just short of aperture 16 (as seen in FIG. 3) is a sampling tube 24. An annular space 25 is provided between sampling tube 24 and the cylindrical wall 26 surrounding outlet port 22. A sample container 28 is removably connected to cylindrical wall 26 so that sampling tube 24 depends into sampling fluid 29 within the sample container. Sample fluid 29 is typically a diluted liquid medium containing particles 30 such as cells or the like which are to be analyzed in conjunction with the apparatus being described. Air, as indicated by the dashed arrows in FIG. 1, flows through air flow channel 15 and out of air outlet port 22 through annular space 25 and into the sample container. It is appreciated that air will flow out of air outlet port 22 if the present apparatus is operating irrespective of whether a sample container is attached thereto.

Air and sheath fluid are provided to chamber 12 by the elements illustrated in FIG. 1. An air pump 40, capable of delivering air at a pressure preferably at approximately 3 psi, delivers air through a pressure regulator 43 and through an air flow line 41 to another air line 42 which is in fluid communication with air channel 15 in the chamber. Pressure regulator 43 serves preferably as an overall system regulator. A fluid resistor 44 is positioned adjacent the interconnection of air flow lines 41 and 42 for the purpose of limiting the air flow into air flow channel 15. A branch air flow line 45 extends from air line 41 through a regulator 46 which is adapted to regulate the pressure through line 45. Preferably, this pressure level is regulated at about 1 psi. Branch line 45 terminates in reservoir 48 which contains a quantity of sheath fluid 50. This sheath fluid should be substantially particle free so that it does not interfere with the analysis of particles 30 in sampling fluid 29; also, sheath fluid 50, in some applications of the present invention, should be capable of carrying an electrical current so that a potential can be applied across aperture 16 for purposes of particle analysis. A saline solution, in these instances, is desirably utilized as the sheath fluid.

Depending into sheath fluid 50 in reservoir 48 is a conduit 51 which is connected at its other end to an antechamber 52. Sheath fluid enters antechamber 52 through an opening 54 located in the bottom of the antechamber in the orientation illustrated in FIG. 1. Sheath fluid exits the antechamber through an opening 55 in the side of the antechamber and then travels through a sheath fluid flow line 56 which is in fluid communication with sheath fluid channel 14 in chamber 12. A fluid resistor 58 is preferably included in sheath fluid flow line 56 for the purposes of regulating the flow of sheath fluid into the chamber, and for effectuating a drop in pressure in the antechamber. Completing the fluid circuit to antechamber 54 is the air flow line 42 which has one end connected to air channel 15 in the chamber, as previously described, and has its other end connected to the antechamber as seen in FIG. 1. Another opening 59 is provided in the antechamber so that there is air flow communication between the antechamber and air flow line 42.

Figure 4:
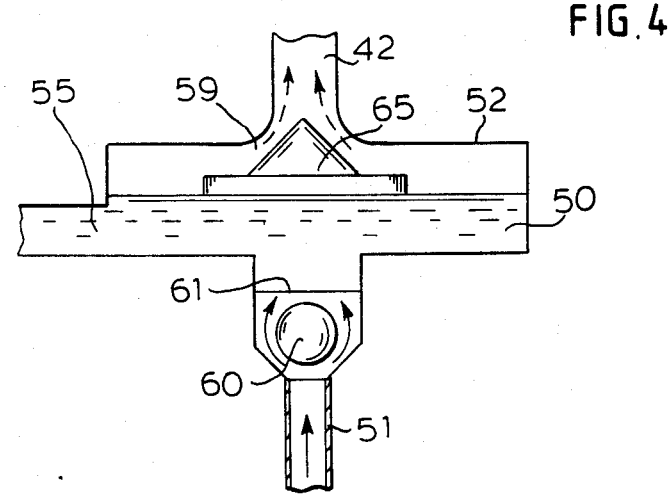
FIG. 4 is an enlarged cross-sectional view of the preferred antechamber as it appears when being filled with sheath fluid.
Figure 5:
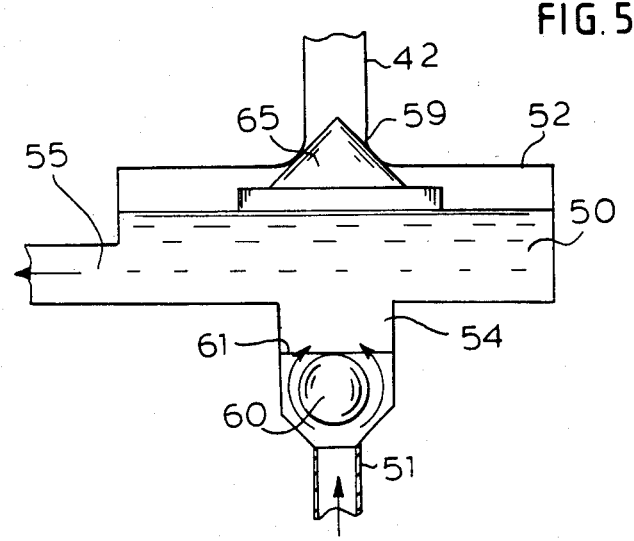
FIG. 5 is an enlarged cross-sectional view of the preferred antechamber of the particle analyzing apparatus when filled with sheath fluid.

Referring now to FIGS. 4 and 5, together with FIG. 1, it can be seen that there are two operable valves associated with antechamber 52. A first valve, preferably a ball valve 60 is associated with opening 54 to which conduit 51 is connected. Ball valve 60 normally has a specific gravity heavier than the sheath fluid and is thus adapted to normally rest on the opening of conduit 51 to maintain the conduit closed. Under pressure of fluid flowing through conduit 51, the ball valve moves away from the conduit and allows sheath fluid to pass through opening 54 into antechamber 52. A retaining wall 61 may be provided to keep the travel of the ball valve to a minimum. On the other hand, although ball valve 60 allows fluid to flow from the sheath fluid reservoir into the antechamber, it also operates to restrict reverse flow if the pressure in the antechamber is higher than the pressure in the reservoir. When sheath fluid 50 is filling antechamber 52, the second valve in the antechamber, a float valve 65 floats at the level of the sheath fluid. As seen more clearly in FIG. 5, when the antechamber is full of sheath fluid, float valve 65 closes against opening 59. This closure prevents sheath fluid from flowing into air line 42 but allows the antechamber to be pressurized and subsequently establish full sheath fluid flow conditions.

In operation, apparatus 10 functions similar to the apparatus described in U.S. Pat. No. 4,240,029. However, in the present invention, the antechamber and related air and fluid flow lines have been added as improvements particularly for regulating and/or controlling the flow of sheath fluid. In particular, apparatus 10 is adapted to run continuously and analyze particles from the sample fluid on an intermittent basis, i.e., a sample fluid container is positioned over the sampling tube for testing and then is removed until another such container is placed in position. Sheath fluid continues to flow even during the time when no sample fluid container is in position on the apparatus, but at a slower flow rate.

First, when no sample container 28 is in position over outlet port 22, pump 40 is operating to pump air through regulator 43 into chamber 12 through air flow channel 15. Air flows out through the air outlet port and into atmosphere since no sample fluid is in position. As a result, there is no back pressure on air line 42 and it and antechamber 52 have an air pressure which is essentially at atmospheric, room pressure. At the same time, air passes through regulator 46 into reservoir 48 at a pressure of approximately 1 psi. This causes sheath fluid 50 to rise through conduit 51, opening ball valve 60, whereupon sheath fluid fills the antechamber. Once the chamber is filled, float valve 65 prevents sheath fluid from flowing into air line 42 while maintaining the pressure of the antechamber at about 1 psi. At this low pressure, sheath fluid flows through flow line 56 into sheath fluid channel 14 in chamber 12. Sheath fluid continues to flow through aperture 16 into flow line 20 whereupon it is collected in container 21. Thus, when no sample is in position, the flow rate of the sheath fluid is very low thereby reducing the consumption of sheath fluid, allowing the use of a smaller reservoir or longer run time before reservoir changes. It is beneficial that the apparatus be allowed to run even when a sample fluid is not present to keep the system in equilibrium and to keep noise low. When a sample is present, it is also important that there be minimum changes in the fluid level in the sheath reservoir of such an apparatus as being described which relies on a hydrodynamically focused flow of fluid therethrough. As pointed out above, variations in the sheath fluid level affect the differential pressure between the sheath fluid and the sample fluid, which in turn, affects the sample flow rate.

When sample container 28 with sample fluid 29 and particles 30 therein is placed in position over air outlet port 22, by virtue of sealably contacting cylindrical wall 26, tubing 24 is submerged in the sample fluid. Accordingly, air provided through air channel 15 pressurizes container 28, and the air flow rate drops by a factor of one hundred or more. The pressure drop in fluid resistor 44 becomes negligible and both container 28 and antechamber 52 come up to the pressure of the air pump, i.e., 3 psi. This pressure causes sample fluid to flow into tube 24 which is directed toward aperture 16. At the same time, since pressure in the antechamber rises to approximately 3 psi, sheath fluid will flow at a greater rate through line 56 and fluid channel 14 in the chamber. Sheath fluid 50 ensheathes the sample fluid with a flowing sheath fluid for hydrodynamically focusing the particles as they pass though aperture 16, as more clearly seen in FIG. 3. Typically, sheath fluid will flow at a rate of about 2 milliliters per minute, which is typically, but not necessarily, forty times the flow rate of the sample fluid. When sample container 28 is in position over outlet port 22, there should be a height differential, designated as $\Delta H$ in FIG. 1, between the levels of fluid in the antechamber and the sample container. While $\Delta H$ is preferably held constant from sample to sample, this height differential may be varied within reasonable limits. This allows the antechamber to maintain proper fluid level and pressure when the apparatus is operating with the sampling fluid connected to chamber 12. In this regard, the present invention maintains a relatively stable and consistent sheath fluid pressure level while the apparatus is operating. Specifically, the hydrostatic fluid pressure of the sheath fluid is determined by the height of fluid in antechamber 52. Since the fluid level in the antechamber changes relatively little during operation, for practical purposes, the pressure of the sheath fluid is substantially constant during operation of the apparatus. Even if small changes are detectable, they would be predictable and always known to the user, since the level of the fluid in the antechamber always starts at the same height at the beginning of operation of the apparatus. The present invention can be readily constructed so that any changes of fluid level in the antechamber are relatively small with respect to the height of the fluid within reservoir 48.

Figure 6:
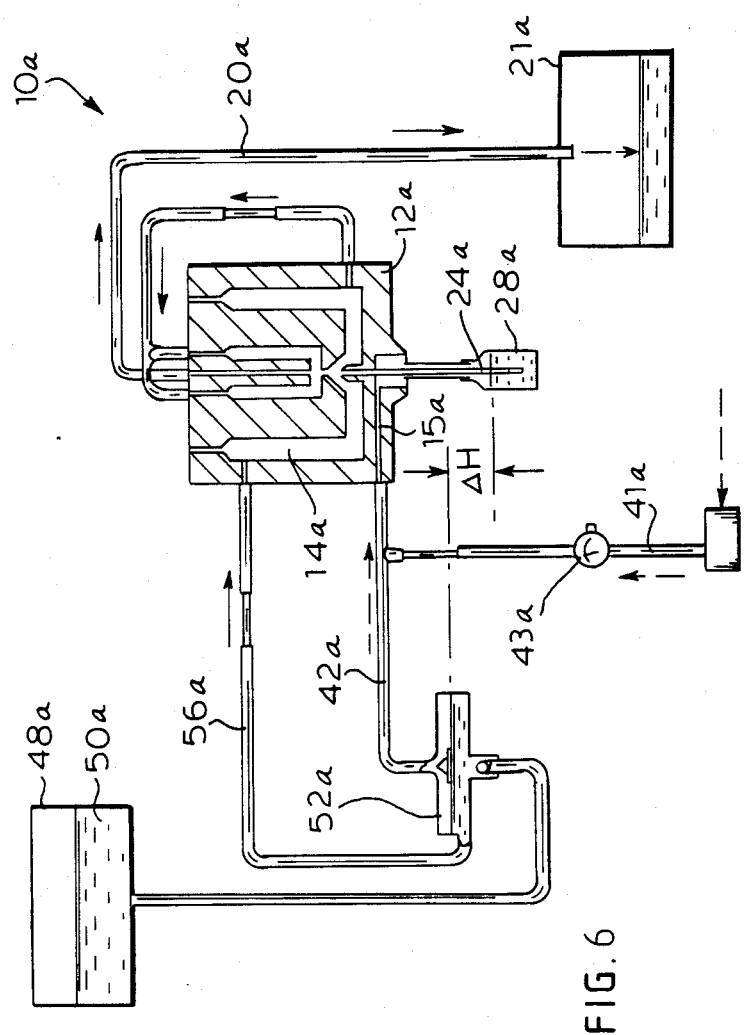
FIG. 6 is a schematic representation of an alternative arrangement of elements in a particle analyzing apparatus providing for gravity feed of the sheath fluid through the antechamber.

Although there may be many modifications within the purview of the present invention, FIG. 6 illustrates one such alternative embodiment. Except for the arrangement of reservoir 48a, and associated fluid lines, all of the elements of apparatus 10a are the same as those illustrated in FIG. 1. In FIG. 6, reservoir 48a has been elevated so that the 1 psi regulator (as included in the embodiment of FIG. 1) can be eliminated. Thus, the low pressure provided to antechamber 52a when no sample is present is implemented by elevating reservoir 48a above antechamber 52a and allowing sheath fluid 50a to flow into the antechamber by gravity. It is understood that other variations may also be employed within the scope of the present invention.

Significantly, the present invention allows the apparatus to operate at two different flow rates for the sheath fluid, and operates so that the sheath fluid pressure is unaffected by the fluid level in the sheath fluid reservoir. Moreover, the valves in the antechamber while self-actuating, need not be critical in design and function. Specifically, if valve 65 should leak, liquid would be forced into the air line when no sample is present, but such liquid would drip out of air outlet port 22 due to the fact that the 3 psi air pressure in the air lines would prevent such liquid from travelling through fluid resistor 44 and into the remaining air lines. On the other hand, if ball valve 60 should leak, then some of the sheath fluid in the antechamber would be pushed back into the sheath reservoir. However, if there is adequate fluid in the antechamber, the small loss of fluid would not be critical.

Thus, the present invention provides an apparatus and method for regulating sheath fluid flow in a hydrodynamically focused fluid flow system. The present apparatus is adapted to operate continuously even in the absence of sampling fluid. Advantageously, sheath fluid in the present apparatus flows at a normal rate compatible with flowing particles when particles are passing through the apparatus for analysis; on the other hand, when no particles are present to be sampled, the apparatus is permitted to operate while sheath fluid flow is substantially reduced thereby minimizing the consumption of sheath fluid. Further, during operation of the present apparatus, the sheath fluid pressure is maintained substantially constant thereby contributing to effective control of the rate of flow of the sheath fluid.

What is claimed is:

1. In a hydrodynamically focused fluid flow system of the type having an aperture through which particles to be analyzed flow, air flow means associated with a sample fluid containing said particles for causing said particles to flow through said aperture, sheath fluid flow means for providing a flow of sheath fluid around said sample fluid for focusing said particles which flow through said aperture, and means for analyzing said particles which flow through said aperture, wherein the improvement comprises:

an antechamber in fluid communication with said air flow means, said sheath fluid flow means and a sheath fluid reservoir containing said sheath fluid, said reservoir also being in fluid communication with said air flow means, said antechamber including a first operable valve which allows sheath fluid to flow from said reservoir to said antechamber but restricts reverse flow if the pressure in the antechamber is higher than the pressure in the reservoir, said antechamber including a second operable valve which closes when the antechamber is full of sheath fluid and prevents sheath fluid from flowing into said air flow means, whereby flow of sheath fluid toward said aperture and flow of air for forcing said particles from the sample fluid through said aperture in a hydrodynamically focused flow are established.

2. The improvement of claim 1 wherein the sheath fluid flow means includes a sheath fluid flow line connected at one end to said antechamber and being in fluid communication with said aperture at its other end.

3. The improvement of claim 1 which further includes a sheath fluid conduit extending between said antechamber and said reservoir, said first valve serving to control flow of sheath fluid through said conduit into and out of said antechamber.

4. The improvement of claim 1 wherein said air flow means includes an air outlet port having a sampling tube extending therethrough in fluid communication with said aperture, said port and said tube adapted to accept a container holding said sample fluid with particles therein to be analyzed, said air flow means further including a first air flow line connected at one end to said antechamber and being in fluid communication with said air outlet port at its other end and including a second air flow line interconnected intermediate of the ends of said first air flow line, the other end of said second air flow line being connected to a pump, and including a third air flow line being connected to said second air flow line, the other end of said third air flow line being in fluid communication with said sheath fluid reservoir.

5. The improvement of claim 4 wherein said second air flow line includes a flow resistor in the area between said first and third air flow lines for limiting the flow or air therethrough.

6. The improvement of claim 4 wherein the third air flow line includes a pressure regulator for regulating the pressure from said pump into said sheath fluid reservoir.

7. The improvement of claim 4 wherein said reservoir is positioned in said system at a higher level than said antechamber so that sheath fluid is adapted to be gravity fed from said reservoir to said antechamber until said antechamber is filled.

8. An apparatus for analyzing particles adapted to operate continuously even in the absence of a sample medium comprising:
a sensing region and particle analyzing means associated therewith;
means for causing a sample medium with particles therein to flow through said sensing region;
means for ensheathing said sample medium with a flowing sheath fluid for hydrodynamically focusing said particles as they pass through said sensing region, said ensheathing means permitting the sheath fluid to flow at a first flow rate compatible with the flow rate of flowing particles; and
means for flowing said sheath fluid at a second flow rate, slower than said first flow rate, when the apparatus is operating in the absence of a sample medium.

9. An apparatus for analyzing particles adapted to operate continuously even in the absence of a sample medium comprising:
a sensing region and particle analyzing means associated therewith;
means for causing a sample medium with particles therein to flow through said sensing region;
means for ensheathing said sample medium with a flowing sheath fluid for hydrodynamically focusing said particles as they pass through said sensing region, said ensheathing means permitting the sheath fluid to flow at a first flow rate compatible with the flow rate of flowing particles and maintaining the pressure of said sheath fluid relatively constant during the analysis of particles when said sheath fluid is flowing at said first flow rate; and
means for flowing said sheath fluid at a second flow rate, slower than said first flow rate, when the apparatus is operating in the absence of a sample medium.

10. In a method for analyzing particles in a hydrodynamically focused fluid flow system including the steps of flowing a sample fluid with particles therein through a sensing region, ensheathing the sample fluid with a flowing sheath fluid for hydrodynamically focusing the particles as they pass through the sensing region and analyzing said particles as they flow through said sensing region, wherein the improvement comprises the steps of:
withdrawing said sheath fluid from a reservoir into an antechamber prior to ensheathing said sample fluid, but preventing the reverse flow toward said reservoir if the pressure in the antechamber is higher than the pressure in the reservoir;
pressurizing said reservoir by pumping air into said reservoir to increase the pressure therein to move sheath fluid through said antechamber and toward said sample fluid;
pumping a flow of air into said sample fluid to cause the sample fluid with particles therein to flow through said sensing region; and
closing the antechamber when it is filled with sheath fluid and preventing sheath fluid from flowing from said antechamber into the flow of air which is directed toward said sample fluid.

11. The method of claim 10 including the step of withdrawing sheath fluid out of said antechamber at a first flow rate when the flow system is operating with a sample fluid for particle analysis and withdrawing sheath fluid out of said antechamber at a second flow rate, slower than first flow rate, when the flow system is operating in the absence of a sample fluid.

12. The method of claim 11 including the step of regulating the pressure to which said reservoir is pressurized by the flow of air therein.

13. The method of claim 12 wherein the regulating step is performed by using a pressure regulator.

14. The method of claim 13 wherein the regulating step is performed by gravity feeding the sheath fluid from the reservoir to the antechamber prior to withdrawing sheath fluid therefrom.

15. A continuously operating method for intermittently analyzing particles comprising:
flowing a sample medium with particles therein through a sensing region;
analyzing said particles for specific characteristics thereof;
ensheathing said sample medium with a flowing sheath fluid for hydrodynamically focusing said particles as they pass through said sensing region, said sheath fluid flowing at a first flow rate compatible with the flow rate of flowing particles; and
flowing said sheath fluid through said sensing region at a second flow rate, slower than said first flow rate, when there is no sample medium being analyzed.

16. A continuously operating method for intermittently analyzing particles comprising:
flowing a sample medium with particles therein through a sensing region;
analyzing said particles for specific characteristics thereof;
ensheathing said sample medium with a flowing sheath fluid for hydrodynamically focusing said particles as they pass through said sensing region, said sheath fluid flowing at a first flow rate compatible with the flow rate of flowing particles maintaining the pressure of said flowing sheath fluid relatively constant during the analysis of particles when said sheath fluid is flowing at said first flow rate; and flowing said sheath fluid through said sensing region at a second flow rate, slower than said first flow rate, when there is no sample medium being analyzed.

* * * * *